(12) United States Patent
Cho et al.

(10) Patent No.: US 11,685,784 B2
(45) Date of Patent: *Jun. 27, 2023

(54) ANTI-IMMUNE-CHECKPOINT NANOBODY AND NUCLEIC ACID ENCODING SEQUENCE THEREOF, AND USES OF THE SAME

(71) Applicant: China Medical University Hospital, Taichung (TW)

(72) Inventors: Der-Yang Cho, Taichung (TW); Shao-Chih Chiu, Taichung (TW); Shi-Wei Huang, Taichung (TW); Chih-Ming Pan, Taichung (TW); Mei-Chih Chen, Taichung (TW); Yu-Chuan Lin, Taichung (TW); Yeh Chen, Taichung (TW)

(73) Assignee: CHINA MEDICAL UNIVERSITY HOSPITAL, Taichung (TW)

(*) Notice: Subject to any disclaimer, the term of this patent is extended or adjusted under 35 U.S.C. 154(b) by 0 days.

This patent is subject to a terminal disclaimer.

(21) Appl. No.: 17/692,701

(22) Filed: Mar. 11, 2022

(65) Prior Publication Data

US 2022/0306746 A1    Sep. 29, 2022

Related U.S. Application Data

(60) Provisional application No. 63/165,274, filed on Mar. 24, 2021.

(51) Int. Cl.
*C07K 16/28*    (2006.01)
*A61K 39/00*    (2006.01)

(52) U.S. Cl.
CPC ...... *C07K 16/2827* (2013.01); *C07K 16/2818* (2013.01); *A61K 2039/505* (2013.01); *C07K 2317/31* (2013.01); *C07K 2317/565* (2013.01); *C07K 2317/732* (2013.01); *C07K 2317/92* (2013.01)

(58) Field of Classification Search
CPC ............ C07K 16/2827; C07K 16/2818; C07K 2317/732; C07K 2317/22; A61K 2039/505
See application file for complete search history.

(56) References Cited

U.S. PATENT DOCUMENTS

2019/0023793 A1*    1/2019   Shen .................... A61K 51/10

FOREIGN PATENT DOCUMENTS

CN    107686520 A    2/2018

* cited by examiner

*Primary Examiner* — Aurora M Fontainhas
*Assistant Examiner* — Jennifer A Benavides
(74) *Attorney, Agent, or Firm* — WPAT, P.C.

(57) ABSTRACT

The present disclosure provides an anti-immune-checkpoint nanobody that specifically binds to a programmed cell death ligand 1. The present disclosure also provides the nucleic acid sequence of the anti-immune-checkpoint nanobody, use of the anti-immune-checkpoint nanobody for treating cancer and immune-related disorders, and a method for detecting expression levels of PD-L1.

19 Claims, 9 Drawing Sheets
(1 of 9 Drawing Sheet(s) Filed in Color)
Specification includes a Sequence Listing.

SEQUENCE LISTING

<160> NUMBER OF SEQ ID NOS: 15

<210> SEQ ID NO 1
<211> LENGTH: 121
<212> TYPE: PRT
<213> ORGANISM: Artificial Sequence
<220> FEATURE:
<223> OTHER INFORMATION: anti-PD-L1 nanobody clone#1

<400> SEQUENCE: 1

```
His Val Gln Leu Val Glu Ser Gly Gly Gly Leu Val Gln Pro Gly Gly
1               5                   10                  15

Ser Leu Arg Ile Ser Cys Ala Ala Ser Gly Phe Thr Phe Ser Ser Arg
            20                  25                  30

Ala Met Ser Trp Val Arg Gln Ala Pro Gly Lys Gly Leu Glu Trp Val
        35                  40                  45

Ser Thr Ile Asn Ser Asp Gly Ser Asn Thr Tyr Tyr Ser Asp Ser Val
    50                  55                  60

Lys Asp Arg Phe Thr Ile Ser Arg Asp Asn Ala Ile Asn Thr Leu Tyr
65                  70                  75                  80

Leu Gln Leu Asn Ser Leu Lys Thr Glu Asp Thr Ala Met Tyr Tyr Cys
                85                  90                  95

Ser Arg Cys Pro Asp Ile Tyr Cys Gly Gly Gln Tyr Thr Tyr Arg Gly
            100                 105                 110

Gln Gly Thr Gln Val Thr Val Ser Ser
        115                 120
```

<210> SEQ ID NO 2
<211> LENGTH: 133
<212> TYPE: PRT
<213> ORGANISM: Artificial Sequence
<220> FEATURE:
<223> OTHER INFORMATION: anti-PD-L1 nanobody clone#14

<400> SEQUENCE: 2

```
His Val Gln Leu Val Glu Ser Gly Gly Gly Ser Val Gln Asn Gly Gly
1               5                   10                  15

Ser Leu Arg Leu Ser Cys Gln Thr Ser Gly Phe Gly Ser Asp Arg Tyr
            20                  25                  30

Glu Ile Gly Trp Tyr Arg Gln Ile Pro Gly Trp Cys Glu Lys Val Ser
        35                  40                  45

Thr Ile Ser Asp Thr Gly Thr Thr Phe Tyr Ala Asp Ser Val Lys Gly
    50                  55                  60

Arg Phe Ala Ile Ser Gln Asp Thr Ala Lys Asn Leu Val Tyr Leu Gln
65                  70                  75                  80

Met Asp Arg Leu Lys Pro Gln Asp Thr Ala Arg Tyr Tyr Cys Ala Ala
                85                  90                  95

Ile Thr Thr Pro Ala Arg Asn Asn Gly Val Leu Asn Ala Leu Ser Arg
            100                 105                 110

Leu Leu Lys Cys Leu Asn Pro Tyr Asn Tyr Trp Gly Gln Gly Thr Gln
        115                 120                 125

Val Thr Val Ser Ser
    130
```

<210> SEQ ID NO 3
<211> LENGTH: 121
<212> TYPE: PRT
<213> ORGANISM: Artificial Sequence
<220> FEATURE:

<223> OTHER INFORMATION: anti-PD-L1 nanobody clone#67

<400> SEQUENCE: 3

Gln Val Gln Leu Val Glu Ser Gly Gly Gly Leu Val Gln Pro Gly Gly
1               5                   10                  15

Ser Leu Arg Ile Ser Cys Ala Ala Ser Gly Phe Thr Phe Ser Ser Arg
            20                  25                  30

Ala Met Ser Trp Val Arg Gln Ala Pro Gly Lys Gly Leu Glu Trp Val
        35                  40                  45

Ser Thr Val Asn Ser Asp Gly Ser Asn Thr Tyr Tyr Ser Asp Ser Val
    50                  55                  60

Lys Asp Arg Phe Thr Ile Ser Arg Asp Asn Ala Ile Asn Thr Leu Tyr
65                  70                  75                  80

Leu Gln Leu Asn Ser Leu Lys Thr Glu Asp Thr Ala Met Tyr Tyr Cys
                85                  90                  95

Ser Arg Cys Pro Asp Ile Tyr Cys Gly Gly Gln Tyr Thr Tyr Arg Gly
            100                 105                 110

Gln Gly Thr Gln Val Thr Val Ser Ser
        115                 120

<210> SEQ ID NO 4
<211> LENGTH: 363
<212> TYPE: DNA
<213> ORGANISM: Artificial Sequence
<220> FEATURE:
<223> OTHER INFORMATION: anti-PD-L1 nanobody clone#1

<400> SEQUENCE: 4
catgtgcagc tggtggagtc tgggggaggc ttggtgcagc ctggggggtc tctgagaatc      60
tcctgtgcag cctctggatt caccttcagt agccgtgcca tgagctgggt ccgccaggct     120
ccagggaagg gactcgagtg ggtctcaacc attaatagtg atggtagtaa cacatactat     180
tcagactccg tgaaggaccg attcaccatc tccagagaca cgccatcaa cacgctgtat      240 ctgcaattga acagcctgaa aactgaggac acggccatgt attactgttc ccgttgtccc     300
gatatttact gcggaggaca atatacgtat cggggccagg ggacccaggt cactgtctcc     360
tca                                                                   363

<210> SEQ ID NO 5
<211> LENGTH: 399
<212> TYPE: DNA
<213> ORGANISM: Artificial Sequence
<220> FEATURE:
<223> OTHER INFORMATION: anti-PD-L1 nanobody clone#14

<400> SEQUENCE: 5
catgtgcagc tggtggagtc tgggggaggc tcggtgcaga tggagggtc tctgcgactc       60 tcctgccaaa cctctggatt tggttctgat cgttatgaaa tcggctggta tcgccaaatt     120
cccggctggt gcgagaaggt ttcaactatc agtgacaccg gcaccacatt ctatgcagac     180
tccgtgaagg gccgcttcgc catctcccaa gacaccgcca gaatctggt atatctgcaa      240 atggacaggt tgaaaccaca ggacacggcc cggtattatt gtgcggctat aaccacccct     300
gccaggaata atggcgtcct gaacgctctg agtcgattat tgaagtgctt aaatccatat     360
aactactggg gccaggggac ccaggtcacc gtctcctca                            399

<210> SEQ ID NO 6
<211> LENGTH: 363

<212> TYPE: DNA
<213> ORGANISM: Artificial Sequence
<220> FEATURE:
<223> OTHER INFORMATION: anti-PD-L1 nanobody clone#67

<400> SEQUENCE: 6

```
caggtgcagc tggtggagtc tgggggaggc ttggtgcagc ctgggggtc tctgagaatc      60
tcctgtgcag cctctggatt caccttcagt agccgtgcca tgagctgggt ccgccaggct    120
ccagggaagg gactcgagtg gtctcaacc gttaatagtg atggtagtaa cacatactat    180
tcagactccg tgaaggaccg attcaccatc tccagagaca cgccatcaa cacgctgtat    240
ctgcaattga atagcctgaa aactgaggac acggccatgt attactgttc ccgttgtccc    300
gatatttact gcggaggaca atatacgtat cggggccagg ggacccaggt cactgtctcc    360
tca                                                                 363
```

<210> SEQ ID NO 7
<211> LENGTH: 8
<212> TYPE: PRT
<213> ORGANISM: Artificial Sequence
<220> FEATURE:
<223> OTHER INFORMATION: CDR1 of anti-PD-L1 nanobody clone#1

<400> SEQUENCE: 7

Gly Phe Thr Phe Ser Ser Arg Ala
1               5

<210> SEQ ID NO 8
<211> LENGTH: 8
<212> TYPE: PRT
<213> ORGANISM: Artificial Sequence
<220> FEATURE:
<223> OTHER INFORMATION: CDR2 of anti-PD-L1 nanobody clone#1

<400> SEQUENCE: 8

Ile Asn Ser Asp Gly Ser Asn Thr
1               5

<210> SEQ ID NO 9
<211> LENGTH: 14
<212> TYPE: PRT
<213> ORGANISM: Artificial Sequence
<220> FEATURE:
<223> OTHER INFORMATION: CDR3 of anti-PD-L1 nanobody clone#1

<400> SEQUENCE: 9

Ser Arg Cys Pro Asp Ile Tyr Cys Gly Gly Gln Tyr Thr Tyr
1               5                   10

<210> SEQ ID NO 10
<211> LENGTH: 9
<212> TYPE: PRT
<213> ORGANISM: Artificial Sequence
<220> FEATURE:
<223> OTHER INFORMATION: CDR1 of anti-PD-L1 nanobody clone#14

<400> SEQUENCE: 10

Thr Ser Gly Phe Gly Ser Asp Arg Tyr
1               5

<210> SEQ ID NO 11
<211> LENGTH: 8
<212> TYPE: PRT
<213> ORGANISM: Artificial Sequence
<220> FEATURE:

```
<223> OTHER INFORMATION: CDR2 of anti-PD-L1 nanobody clone#14

<400> SEQUENCE: 11

Thr Ile Ser Asp Thr Gly Thr Thr
1               5

<210> SEQ ID NO 12
<211> LENGTH: 28
<212> TYPE: PRT
<213> ORGANISM: Artificial Sequence
<220> FEATURE:
<223> OTHER INFORMATION: CDR3 of anti-PD-L1 nanobody clone#14

<400> SEQUENCE: 12

Ala Ala Ile Thr Thr Pro Ala Arg Asn Asn Gly Val Leu Asn Ala Leu
1               5                   10                  15

Ser Arg Leu Leu Lys Cys Leu Asn Pro Tyr Asn Tyr
            20                  25

<210> SEQ ID NO 13
<211> LENGTH: 8
<212> TYPE: PRT
<213> ORGANISM: Artificial Sequence
<220> FEATURE:
<223> OTHER INFORMATION: CDR1 of anti-PD-L1 nanobody clone#67

<400> SEQUENCE: 13

Gly Phe Thr Phe Ser Ser Arg Ala
1               5

<210> SEQ ID NO 14
<211> LENGTH: 8
<212> TYPE: PRT
<213> ORGANISM: Artificial Sequence
<220> FEATURE:
<223> OTHER INFORMATION: CDR2 of anti-PD-L1 nanobody clone#67

<400> SEQUENCE: 14

Val Asn Ser Asp Gly Ser Asn Thr
1               5

<210> SEQ ID NO 15
<211> LENGTH: 14
<212> TYPE: PRT
<213> ORGANISM: Artificial Sequence
<220> FEATURE:
<223> OTHER INFORMATION: CDR3 of anti-PD-L1 nanobody clone#67

<400> SEQUENCE: 15

Ser Arg Cys Pro Asp Ile Tyr Cys Gly Gly Gln Tyr Thr Tyr
1               5                   10
```

ANTI-IMMUNE-CHECKPOINT NANOBODY AND NUCLEIC ACID ENCODING SEQUENCE THEREOF, AND USES OF THE SAME

CROSS-REFERENCE TO RELATED APPLICATION

This application claims priority of Provisional Application No. 63/165,274, filed on Mar. 24, 2021, the content of which is incorporated herein in its entirety by reference.

BACKGROUND OF THE INVENTION

1. Field of the Invention

The present invention relates to an anti-immune-checkpoint nanobody and nucleic acid encoding sequences thereof, and uses of the same.

2. The Prior Art

Cancer, also known as malignancy, is a state of abnormal proliferation of cells, and these proliferating cells may invade other parts of the body as a disease caused by a malfunction in the control of cell division and proliferation. The number of people suffering from cancer worldwide has a growing trend. Cancer is one of the top ten causes of death for the Chinese people and has been the top ten causes of death for consecutive years.

Conventional cancer treatments include surgery, radiation therapy, chemotherapy, and target therapy. Cancer immunotherapy is another method for treating cancer except the above methods. The immune system of the patient is activated in the cancer immunotherapy by using tumor cells or tumor antigens to induce specific cellular and humoral immune responses for enhancing the anti-cancer ability of the patient, preventing the growth, spread, and recurrence of tumors, and achieving the purpose of removing or controlling tumors. However, the current tumor treatments still have the problems of ineffectiveness and strong side effects, and even lead to other immune-related disorders.

Programmed cell death ligand 1 (PD-L1) has been found to be expressed on the cell surface of a variety of solid tumors. Therefore, researchers have been committed to developing PD-L1 as target molecules for tumor identification and to find out whether these target molecules have the potential to become anticancer drugs.

In order to solve the above-mentioned problems, those skilled in the art urgently need to develop a novel and effective medicament for treating cancer and immune-related disorders for the benefit of a large group of people in need thereof.

SUMMARY OF THE INVENTION

A primary objective of the present invention is to provide an anti-immune-checkpoint nanobody that specifically binds to a programmed cell death ligand 1 (PD-L1), comprising an amino acid sequence selected from the group consisting of: SEQ ID NO:1, SEQ ID NO:2, SEQ ID NO:3, and any combination thereof.

According to an embodiment of the present invention, the amino acid sequence is an amino acid sequence of a heavy chain variable domain (VHH) of the anti-immune-checkpoint nanobody.

According to an embodiment of the present invention, the anti-immune-checkpoint nanobody is conjugated with a fragment crystallizable region (Fc region).

According to an embodiment of the present invention, the anti-immune-checkpoint nanobody is conjugated with a second antibody to form a bispecific T-cell engager (BiTE), triple specific T-cell engager (TriTE), bispecific killer cell enager (BiKE), triple specific killer cell engager (TriKE), or any bispecific antibody.

According to an embodiment of the present invention, the anti-immune-checkpoint nanobody blocks interaction and/or binding of the PD-L1 with a receptor of the PD-L1.

According to an embodiment of the present invention, the receptor is programmed cell death protein-1 (PD-1).

Another objective of the present invention is to provide an isolated nucleic acid encoding the above mentioned anti-immune-checkpoint nanobody, wherein the isolated nucleic acid comprises a nucleotide sequence selected from the group consisting of: SEQ ID NO:4, SEQ ID NO:5, SEQ ID NO:6, and any combination thereof.

Another objective of the present invention is to provide a pharmaceutical composition, comprising the above mentioned anti-immune-checkpoint nanobody and a pharmaceutically acceptable carrier.

Another objective of the present invention is to provide a method for treating cancer and immune-related disorders, comprising administering to a subject in need thereof the above mentioned pharmaceutical composition.

Another objective of the present invention is to provide a method for detecting expression levels of PD-L1, comprising administering to a biological sample the above mentioned anti-immune-checkpoint nanobody.

According to an embodiment of the present invention, the biological sample is blood, urine, sputum, saliva or body fluid.

In summary, the anti-immune-checkpoint nanobody of the present invention has the following effect. The anti-PD-L1 nanobody effectively binds to PD-L1 protein within the $K_D$ as 0.27 and 0.41 nM, respectively, by surface plasmon resonance binding assay (SPR binding assay), blocks PD-L1/PD-1 signaling in the PD-L1, APC/PD-1 effector co culture system (the PD-L1/PD-1 axis blockade of the anti-PD-L1 nanobody is determined by PD-1/PD-L1 Blockade Bioassay kit), enhances γδ T cell-induced cytotoxicity to tumor cells (MDA-MB-231), restores OKT3 (anti-CD3 monoclonal antibody)-induced T cell perliferation after PD-L1 engagement by Western blotting, and can be used to detect the expression of PD-L1 in cell samples by flow cytometry analysis and immunocytochemistry analysis, thereby achieving the effect of treating cancer and immune-related disorders. In particular, compared with the conventional antibodies, which have the disadvantages of low yield and poor effect, the gene must be transfected into cells by a vector to express the antibody function, the anti-immune-checkpoint nanobody of the present invention can be prepared in vitro on a large scale, and directly administered to the individual in need for treatment. In addition, the present invention can also achieve the effect of detecting the expression level of PD-L1.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

Figure 1A:
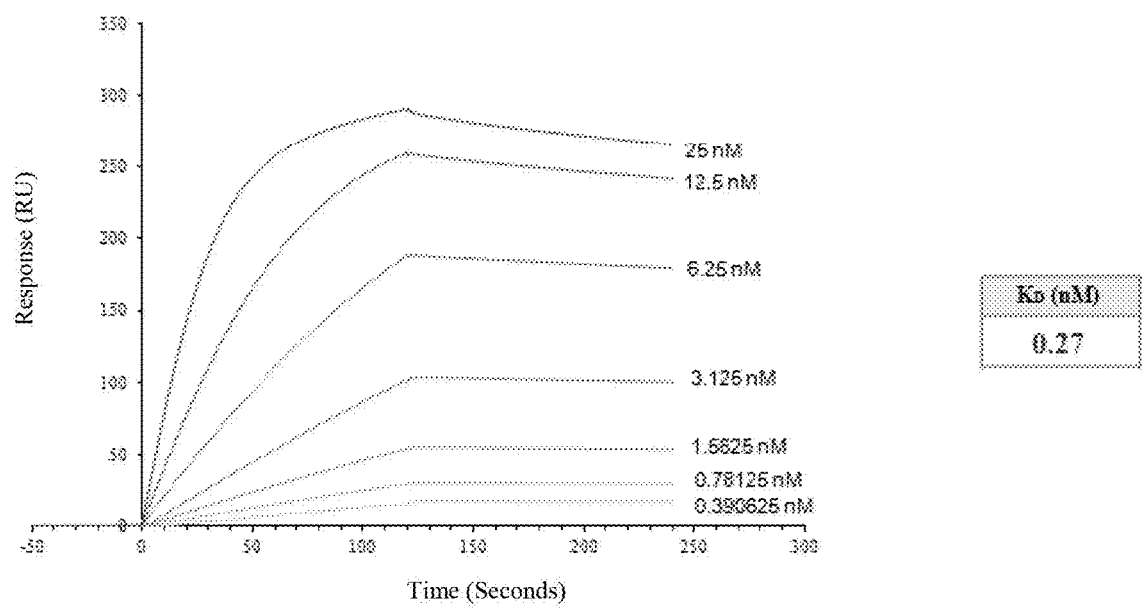
FIGS. 1A and 1B show the surface plasmon resonance binding assay (SPR binding assay) result of the anti-PD-L1 nanobody, wherein nb represents nanobody, RU represents response unit, coated PD-L1 recombination protein (Sino Biological, Cat: 10084-H05H) CM5 chip.

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

As used herein, the terms "anti-programmed cell death ligand 1 (PD-L1) nanobody (NB)" and "anti-immune-checkpoint nanobody" can be used interchangeably.

As used herein, the term "second antibody" refers to the antibody conjugated with the nanobody to form a bispecific T-cell engager (BiTE), triple specific T-cell engager (TriTE), bispecific killer cell enager (BiKE), triple specific killer cell engager (TriKE), or any bispecific antibody. Preferably, the second antibody includes, but is not limited to, anti-CD3ε antibody, anti-human leukocyte antigen-G (HLA-G) antibody, anti-programmed cell death ligand 2 (PD-L2) antibody, anti-T-cell immunoglobulin domain and mucin domain 3 (Tim3) antibody, anti-epidermal growth factor receptor (EGFR) antibody, anti-EGFRvIII antibody, anti-human epidermal growth factor receptor 2 (Her2) antibody, anti-B-cell maturation antigen (BCMA) antibody, anti-CD19 antibody, anti-CD20 antibody, anti-CD34 antibody, anti-CD16 antibody, Fc, anti-epithelial cell adhesion molecule (EpCAM) antibody, anti-mesothelin antibody, anti-New York esophageal squamous cell carcinoma-1 (NY-ESO-1) antibody, anti-glycoprotein 100 (gp100) antibody, and anti-Muc1 antibody.

As used herein, the term "treating" or "treatment" refers to alleviating, reducing, ameliorating, relieving or controlling one or more clinical signs of a disease or disorder, and lowering, stopping, or reversing the progression of severity regarding the condition or symptom being treated.

According to the present invention, the pharmaceutical composition can be manufactured to a dosage form suitable for parenteral or oral administration, using techniques well known to those skilled in the art, including, but not limited to, injection (e.g., sterile aqueous solution or dispersion), sterile powder, tablet, troche, lozenge, pill, capsule, dispersible powder or granule, solution, suspension, emulsion, syrup, elixir, slurry, and the like.

The pharmaceutical composition according to the present invention may be administered by a parenteral route selected from the group consisting of: intraperitoneal injection, subcutaneous injection, intraepidermal injection, intradermal injection, intramuscular injection, intravenous injection, and intralesional injection.

According to the present invention, the pharmaceutical composition may further comprise a pharmaceutically acceptable carrier which is widely used in pharmaceutically manufacturing techniques. For example, the pharmaceutically acceptable carrier can comprise one or more reagents selected from the group consisting of solvent, emulsifier, suspending agent, decomposer, binding agent, excipient, stabilizing agent, chelating agent, diluent, gelling agent, preservative, lubricant, absorption delaying agent, liposome, and the like. The selection and quantity of these reagents fall within the scope of the professional literacy and routine techniques of those skilled in the art.

According to the present invention, the pharmaceutically acceptable carrier comprises a solvent selected from the group consisting of water, normal saline, phosphate buffered saline (PBS), sugar-containing solution, aqueous solution containing alcohol, and combinations thereof.

As used herein, the term "nucleic acid", "nucleic acid sequence" or "nucleic acid fragment" refers to a sequence of deoxyribonucleotides or ribonucleotides in single- or double-stranded forms, and comprises known naturally occurring nucleotides or artificially chemical mimics. As used herein, the term "nucleic acid" is used interchangeably with the terms "gene", "cDNA", "mRNA", "oligonucleotide" and "polynucleotide".

Example 1

Preparation of Anti-PD-L1 Nanobody

In this example, the preparation process of the anti-programmed cell death ligand 1 (PDL-1) nanobody (NB) is as follows. The heavy chain variable domain (VHH) production protocol is as follows. The VHH gene was constructed in expression vector pET22b (Amp resistance) or pSB-init (CmR resistance); The plasmid was identified by restriction enzyme digestion and sequenced verification. 1 µL identified plasmid (about 50 ng) was added to BL21 (DE3), and incubated overnight at 37° C. LB culture medium containing resistance was inoculated with a single colony and the cultures were incubated overnight at 37° C., 220 r/min Overnight culture was inoculated in a fresh LB medium (10 L-20 L) containing resistance at a ratio of 1:100, and cultured at 37° C. and 220 r/min. It was cooled to room temperature when the $OD_{600}$ reaches 0.8. Isopropyl-β-D-thiogalactopyranoside (IPTG) was added with a final concentration of 0.1 mM and induced overnight at 20° C., 220 r/min. The cells and supernatant were harvested after cell disruption by centrifugation (20 mM Tris pH8.0, 150 mM NaCl). Supernatant was combined with Ni-NTA beads (1 mL) by flow-through. The Ni-NTA beads were washed and eluted with buffers containing suitable gradient imidazole (10 mM, 20 mM, 50 mM, 100 mM, 250 mM and 500 mM). Elution fraction was analyzed by SDS-PAGE, and the subsequent purification scheme was determined according to the purity and yield of the protein (ion exchange chromatography or gel filtration chromatography). The protein that meets the requirements was separated and purified by gel filtration chromatography, and buffer was replaced with PBS buffer. The protein component was analyzed by SDS-PAGE, the components were merged and concentrated that meet the requirements, filtered with 0.22 µm filter and aliquot. The protein was stored at −20° C. or lower.

The Production and purification of nanobodies are from E. coli. For producing nanobody form E. coli is modified in view of Microb Cell Fact. 2019 Mar. 11; 18(1):47. In brief, the E. coli strain HB2151 was used. The plasmid pET (Creative Biolab) coding an ampicillin resistance was used for cytoplasmic protein production. Freshly transformed E. coli HB2151 with PD-L1 or PD-L1 multispecific nanobody plasmids would be inoculated in 5 mL of media containing 50 µg/mL of ampicillin and cultivated at 37° C. for overnight. After that, 1 mL of this pre-culture was inoculated into 100 mL medium and grown at 37° C. After overnight cultivation, two EnPresso booster tablets and an additional dose of the glucose releasing enzyme (0.6 U/L) would be added to each 100 mL culture. At the same time, recombinant nanobody protein expression would be induced by the addition of 1 mM IPTG continued as for 24 hours. Then the cultures would be collected and chilled on ice for 5 min and centrifuged for 15 min at 6,000×g and 4° C. After removal of the supernatant, the cell pellets would be purified by high-capacity Myc-tag binding resin using immobilized metal affinity chromatography (IMAC). The gravity-flow-based chromatography would be carried out under native conditions according to the manufacturer protocol (Clontech Laboratories). Efficient cell lysis would be achieved by addition of 1 mL xTractor cell lysis buffer (Clontech Laboratories) supplemented with EDTA-free protease inhibitor cocktail (Roche Diagnostics) and 25 U endonuclease (Thermo Scientific Pierce) to each 200 mg bacterial cell pellet. After incubation on ice for 15 min and centrifugation at 10,000×g and 4° C. for 20 min for removal of cellular debris, the clarified supernatant would be loaded onto a gravity-flow column containing 1 mL of prepacked resin and incubated at room temperature for 30 min. Before elution of the nanobodies by addition of elution buffer containing 300 mM imidazole, the column would be washed twice with increasing imidazole concentrations of 20 and 40 mM. Removal of imidazole and buffer exchange would be achieved by dialysis against PBS using a cellulose ester membrane with a molecular weight cut-off of 3.5-5 kDa (Spectrum® Laboratories).

The alignment and amino acid sequences of the complementarity determining regions (CDRs) for each clone of anti-PD-L1 nanobodies are shown in Table 1. The amino acid sequence of anti-PD-L1 nanobody clone #1 is SEQ ID NO:1; The amino acid sequence of anti-PD-L1 clone #14 is SEQ ID NO:2; The amino acid sequence of anti-PD-L1 clone #67 is SEQ ID NO:3; The nucleotide sequence encoding the amino acid sequence of anti-PD-L1 clone #1 is SEQ ID NO:4; The nucleotide sequence encoding the amino acid sequence of anti-PD-L1 clone #14 is SEQ ID NO:5; The nucleotide sequence encoding the amino acid sequence of anti-PD-L1 clone #67 is SEQ ID NO:6.

TABLE 1

| Clone | CDR1 | CDR2 | CDR3 |
|-------|------|------|------|
| #1 | GFTFSSRA (SEQ ID NO: 7) | INSDGSNT (SEQ ID NO: 8) | SRCPDIYCGGQYTY (SEQ ID NO: 9) |
| #14 | TSGFGSDRY (SEQ ID NO: 10) | TISDTGTT (SEQ ID NO: 11) | AAITTPARNNGVLNALSRLL KCLNPYNY (SEQ ID NO: 12) |
| #67 | GFTFSSRA (SEQ ID NO: 13) | VNSDGSNT (SEQ ID NO: 14) | SRCPDIYCGGQYTY (SEQ ID NO: 15) |

Example 2

Surface Plasmon Resonance Binding Assay (SPR Binding Assay) Result of Anti-PD-L1 Nanobody In this example, the procedures of the surface plasmon resonance binding assay (SPR binding assay) result of the anti-PD-L1 nanobody are as follows. The CM5 or NTA chip, research grade would be performed for SPR analysis by BIAcore T200 (Biacore-GE Healthcare, Piscataway, N.J.). Briefly, protein (HLA-G, PD-L1 or CD3☐/CD3☐ recombinant protein) sample was diluted in the 10 mM buffer solutions (pH 4.0, 5.5 or 6.0) at the concentration range of 20 µg/mL to give maximum surface retention for immobilization on the chip, following the SURFACE PREPATRATION process and choosing the condition of higher surface concentration of ligands (PD-L1 or PD-L1 multispecific nanobodies, 25, 12.5, 6.25, 3.125, 1.5625 and 0.78125 nM) on the chip. Then the regeneration scouting and surface performance test, following REGENERATION SCOUTING and SURFACE PERFORMANCE TEST and then REGENERATION METHOD was selected to run the experiment. And then BINDING ANALYSIS and DIRECT BINDING were selected to investigate protein binding. The KINETIC ANALYSIS would be selected and choose MASS TRANSFER was chosen to run kinetic assay accompany with binding experiment. Data analysis and kinetic constants were determined.

Figure 1B:
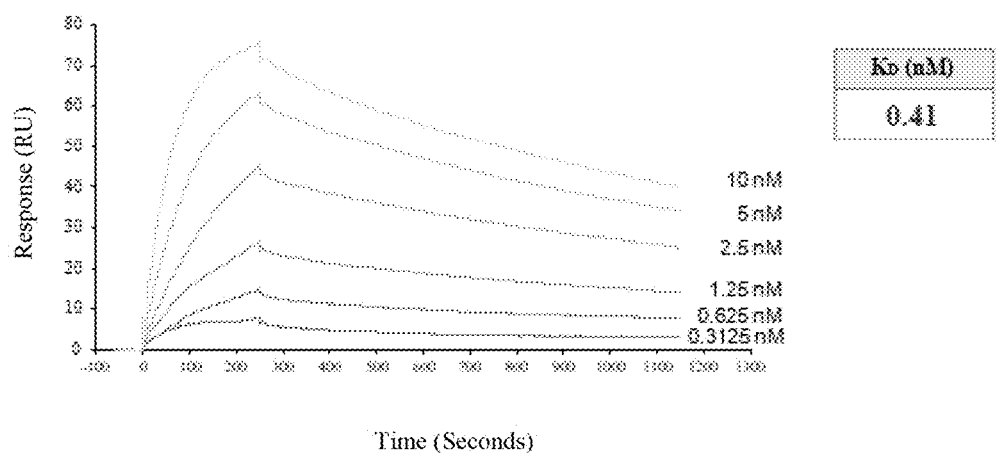

The result of SPR binding assay of the anti-PD-L1 nanobody is shown in FIGS. 1A and 1B, wherein nb represents nanobody, and RU represents response unit. As shown in FIGS. 1A and 1B, the anti-PD-L1 nanobody effectively binds to PD-L1 protein within the $K_D$ as 0.27 and 0.41 nM, respectively.

Example 3

PD-L1/PD-1 Axis Blockade of Anti-PD-L1 Nanobody is Determined by PD-1/PD-L1 Blockade Bioassay kit In this example, the procedures of the PD-L1/PD-1 axis blockade of the anti-PD-L1 nanobody determined by PD-1/PD-L1 Blockade Bioassay kit are as follows. $1 \times 10^4$ of PD-L1 aAPC/CHO-K1 Cells were plating on 96-well plate overnight. Next day, the $1 \times 10^4$ of PD-1 effector cells were added into the wells containing PD-L1 aAPC/CHO-K1 cells. Different concentrations of anti-PD-L1 nanobody (clone #1 or clone #67) or Atezolizumab were added, wherein Atezolizumab is a monoclonal antibody medication used to treat urothelial carcinoma, non-small cell lung cancer (NSCLC), triple-negative breast cancer (TNBC), small cell lung cancer (SCLC), and hepatocellular carcinoma (HCC), and it is a fully humanized, engineered monoclonal antibody of IgG1 isotype against the protein programmed cell death-ligand 1 (PD-L1). After 6 hr, Bio-Glo™ reagent was added and luminescence measured using the GloMax® Discover System. Data were fitted to a 4PL curve using Sigmaplot software.

Figure 2:
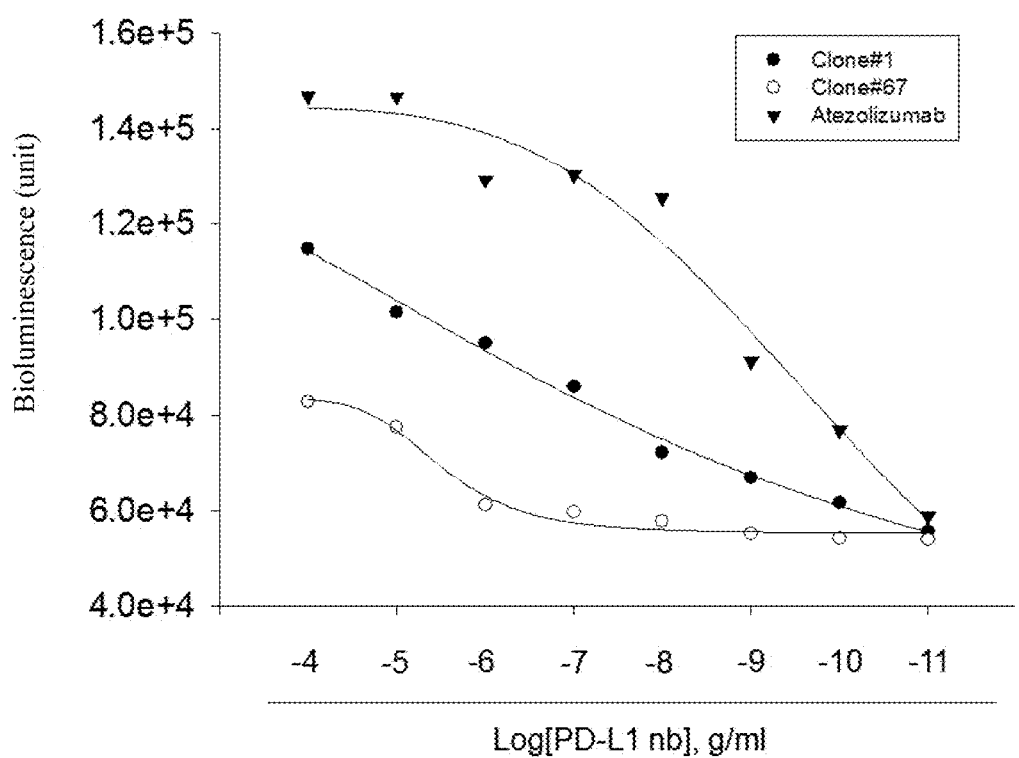
FIG. 2 shows that the PD-L1/PD-1 axis blockade of the anti-PD-L1 nanobody is determined by PD-1/PD-L1 Blockade Bioassay kit, wherein PD-L1 nb represents anti-PD-L1 nanobody, Atezolizumab is a monoclonal antibody medication used to treat urothelial carcinoma, non-small cell lung cancer (NSCLC), triple-negative breast cancer (TNBC), small cell lung cancer (SCLC), and hepatocellular carcinoma (HCC), and it is a fully humanized, engineered monoclonal antibody of IgG1 isotype against the protein programmed cell death-ligand 1 (PD-L1).

The result of this example is shown in FIG. 2, wherein Atezolizumab is a monoclonal antibody medication used to treat urothelial carcinoma, non-small cell lung cancer (NSCLC), triple-negative breast cancer (TNBC), small cell lung cancer (SCLC), and hepatocellular carcinoma (HCC), and it is a fully humanized, engineered monoclonal antibody of IgG1 isotype against the protein programmed cell death-ligand 1 (PD-L1). As shown in FIG. 2, anti-PD-L1 nanobodies clone #1 and clone #67 block PD-L1/PD-1 signaling in the PD-L1, APC/PD-1 effector co culture system.

Example 4

Result of T Cell Proliferation Assay of Anti-PD-L1 Nanobody

In this example, the procedures of T cell (i.e., peripheral blood mononuclear cell (PBMC)) proliferation assay of the anti-PD-L1 nanobody are as follows. $1 \times 10^6$ of PBMC cells were plating on 12-well plate presence with or without recombinant human PD-L1 (10 µg/ml, Sino Biological, Cat: 10084-H05H). 1 µg/ml of anti-PD-L1 nanobody (clone #1 or clone #67) was added. After 7 days, the total cell numbers were recorded, then stained with FITC-conjugated CD3 monoclonal antibody (Cat #11-0037-42) and then analyzed by flow cytometry. The CD3 positive cells were calculated as % of CD3 cells×total cell number, CD3 monoclonal antibody alone group set as 100%.

Figure 3:
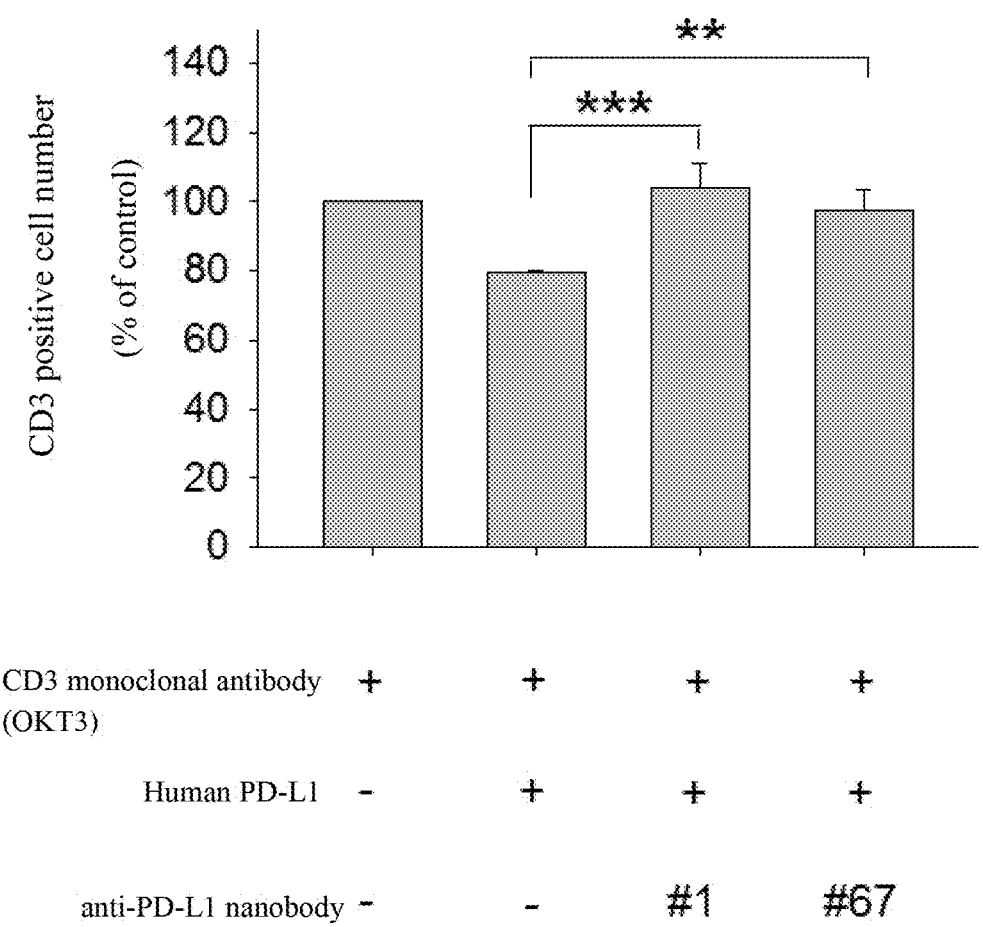
FIG. 3 shows the result of T cell proliferation assay of the anti-PD-L1 nanobody, wherein  represents $p<0.01$; * represents $p<0.001$.

The result of T cell proliferation assay of the anti-PD-L1 nanobody is shown in FIG. 3, wherein  represents p<0.01; * represents p<0.001. As shown in FIG. 3, anti-PD-L1 nanobodies clone #1 and #67 enhance γδT cell-induced cytotoxicity to tumor cells (MDA-MB-231).

Example 5

Evaluation of Effect of Anti-PD-L1 Nanobody on Enhancing γδ T (GDT) Cell-Induced Cytotoxicity to Human Breast Cancer Cell Line MDA-MB-231

In this example, effect of anti-PD-L1 nanobody on enhancing γδ T (GDT) cell-induced cytotoxicity to human breast cancer cell line MDA-MB-231 (purchased from American Type Culture Collection (ATCC)) is evaluated. The procedure is as follows. Peripheral blood mononuclear cells (PBMCs), natural killer (NK) or γδ T cells would be used as effector cells. Target cells (tumor cell lines) would be cocultured with the effector cells at the indicated ratios of effector/target (E:T) from 1:1 to 50:1 for 24 to 72 hours at 37° C. For the Live/Dead Cell Viability Assay, all the tumor cells would be stained with green-fluorescent calcein-AM before coculture, and then staining with red-fluorescent ethidium homodimer-1 after coculture would be used to label the dead cells, the dead tumor cells would be determined as green-fluorescent+/red-fluorescent+ cells according to the manufacturer's instructions (Thermo Fisher Scientific). The cell killing rates are presented as the percentages of the total cell population.

The procedures regarding expansion of primary γδT cells are as follows. Human PBMCs ($1 \times 10^7$) would be cultured for 2 weeks in X-VIVO15 medium (Lonza, Basel, Switzerland) containing zoledronic acid (5 µM) and 1000 IU/ml IL-2 and supplemented with 10% platelet-rich plasma (PRP). The cell number would be recorded, and the purity and potency would be determined by flow cytometry using fluorescence conjugated CD3, Vγ9, Vδ2 and NKG2D antibodies.

The procedures regarding expansion of primary natural killer (NK) cells are as follows. Human NK cells would be isolated from PBMCs by negative selection kits according to the manufacturer's instructions (STEMCELL Technologies Vancouver Canada). NK cells would be cultured for 3 weeks in X-VIVO15 medium (Lonza, Basel, Switzerland) containing CD355 and CD2 antibodies (Miltenyi Biotec, Bergisch Gladbach, Germany) plus 500 IU/ml IL-2 (PeproTech, Rocky Hill, USA) and supplemented with 10% platelet-rich plasma (PRP). The cell number would be recorded, and the purity would be determined by flow cytometry using fluorescence conjugated CD56 and CD16 antibody for NK cells.

$1 \times 10^5$ of MDA-MB-231 cells were plating on 12-well plate overnight. Next day, the $3 \times 10^5$ of primary γδT cells were added into the wells containing MDA-MB-231 cells. 1 µg/ml of anti-PD-L1 nanobody (clone #1 or clone #67) or 10 µg/ml Atezolizumab was added. After 48 hr, the specific lysis to MDA-MB-231 cells by primary γδT cells were determined by LIVE/DEAD cell-mediated cytotoxicity assay using flow cytometry analysis.

Figure 4:
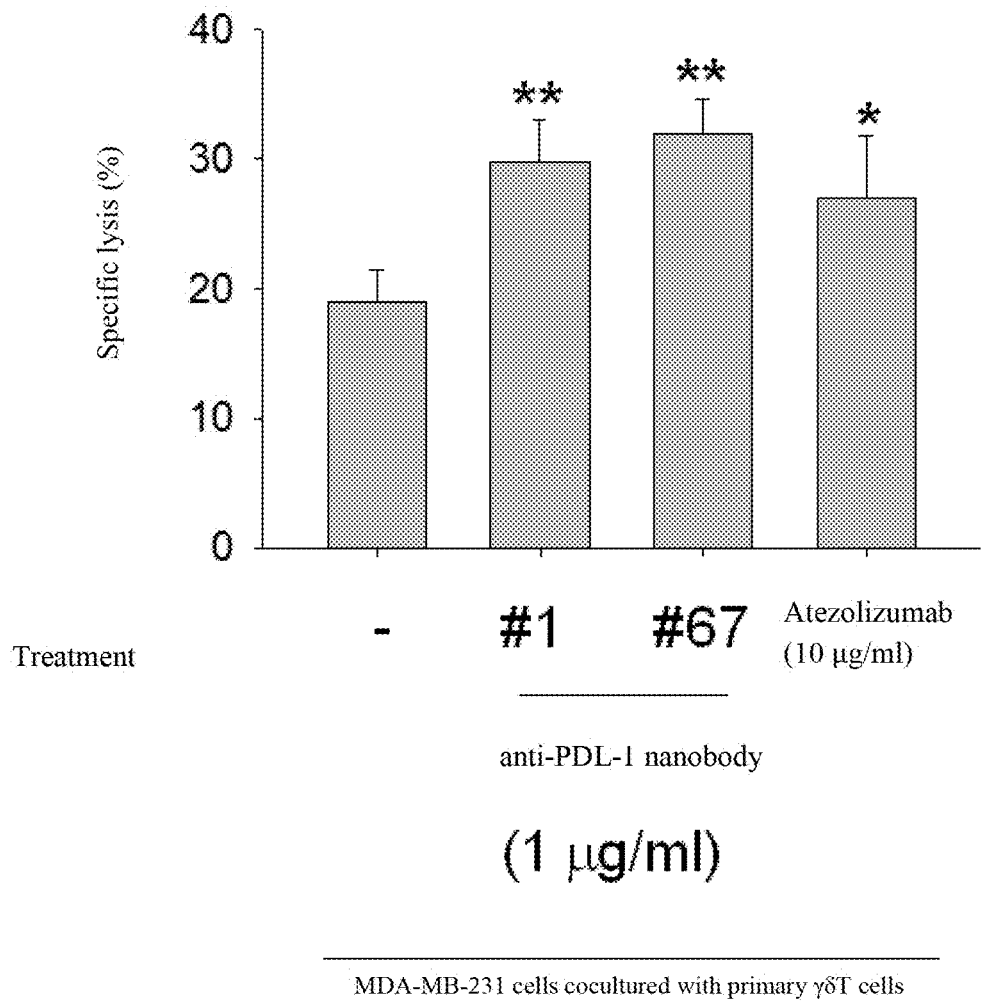
FIG. 4 shows that the anti-PD-L1 nanobody enhances γδ T (GDT) cell-induced cytotoxicity to human breast cancer cell line MDA-MB-231, wherein the leftmost group represents the γ-δ T cell-treated group alone, not merged with any antibody; * represents $p<0.05$; ** represents $p<0.01$.

The result of the anti-PD-L1 nanobody on enhancing γδ T (GDT) cell-induced cytotoxicity to human breast cancer cell line MDA-MB-231 is shown in FIG. 4, wherein the leftmost group represents the γδ T cell-treated group alone, not merged with any antibody; * represents p<0.05; ** represents p<0.01. The result in this example shows that the anti-PD-L1 nanobody enhances γδ T (GDT) cell-induced cytotoxicity to tumor cells (MDA-MB-231).

Example 6

Western Blotting Result of Anti-PD-L1 Nanobody

In this example, the procedures of Western blotting for anti-PD-L1 nanobody are as follows. Cells would be harvested in PRO-PREP protein extraction solution (iNtRON, Taipei, Taiwan) containing a protease inhibitor cocktail and vigorously shaken at 4° C. for 15 min, followed by centrifugation. The supernatants would be collected then the protein concentrations were determined by using the Bio-Rad BCA reagent (Bio-Rad Hercules, Calif., USA). A 30 μg of each sample lysate would be subjected to electrophoresis on SDS-polyacrylamide gels then electroblotted onto PVDF membranes. After 5% BSA in TBST blocking, the membranes would be incubated with primary antibodies in TBST at 4° C. overnight. They would be then washed 4 times and incubated with horseradish peroxidase (HRP)-conjugated goat anti-mouse or rabbit IgG (Upstate, Billerica, Mass., USA) for 2 hours. After washing with TBST 4 times, the blots would be incubated for 1 min with the SuperSignal West Pico ECL reagent (Pierce Biotechnology, Rockford, Ill., USA), and chemiluminescence would be detected using by exposure to Kodak-X-Omat film.

Figure 5:
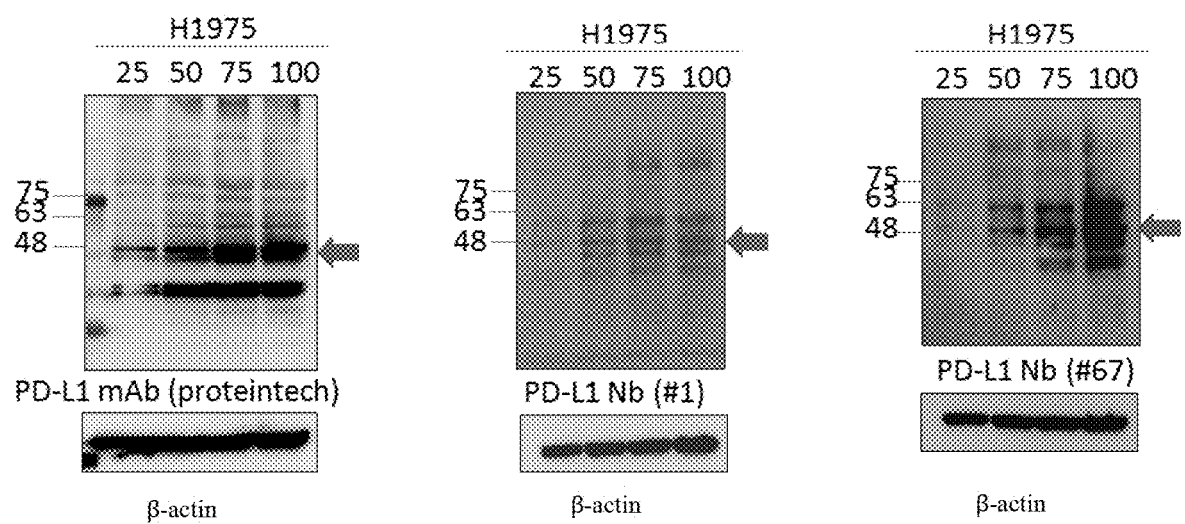
FIG. 5 shows the result of Western blotting analysis of the anti-PD-L1 nanobody, wherein the arrows indicate PD-L1 protein positions, molecular weight consistent with commercial antibodies; the used cell line is non-small cell lung cancer cell line H1975 (NCI-H1975 [H-1975, H1975], ATCC), the commercial antibody is PD-L1 monoclonal antibody (66248-1-Ig, Proteintech), the primary antibody of the commercial antibody group (1:2500), the secondary antibody is anti-rabbit-horseradish peroxidase (anti-Rab-HRP)(1:10000); the concentration of the anti-PD-L1 nanobody of the experimental group is 1 ng/ml, the secondary antibody is anti-VHH-HRP (1:10000).

The result of Western blotting analysis of the anti-PD-L1 nanobody is shown in FIG. 5, wherein the arrows indicate PD-L1 protein positions, molecular weight consistent with commercial antibodies; the used cell line is non-small cell lung cancer cell line H1975 (NCI-H1975 [H-1975, H1975], ATCC), the commercial antibody is PD-L1 monoclonal antibody (66248-1-Ig, Proteintech), the primary antibody of the commercial antibody group (1:2500), the secondary antibody is anti-rabbit-horseradish peroxidase (anti-Rab-HRP)(1:10000); the concentration of the anti-PD-L1 nanobody of the experimental group is 1 ng/ml, the secondary antibody is anti-VHH-HRP (1:10000). The result of this example shows that anti-PD-L1 nanobodies clone #1 and #67 restore OKT3 (anti-CD3 monoclonal antibody)-induced T cell perliferation after PD-L1 engagement.

Example 7

Result of Flow Cytometric Analysis of Anti-PD-L1 Nanobody

In this example, the procedures of flow cytometric analysis of the anti-PD-L1 nanobody are as follows. The anti-PD-L1 nanobody (1 ng/ml) was pre-stained with FITC fluorescein by Fastlink Fluorescein Labeling Kit (Abnova), the procedures were performed according to the manual instructions. MDA-MB-231, A549 or H1975 cells were stained with FITC-conjugated PD-L1 monoclonal antibody (1:500, BD Pharmingen, clone MIH1, Cat: 558065) or FITC-conjugated anti-PD-L1 nanobody (1 ng/ml) for 45 min in PBS containing 1% BSA. After washing with PBS, the cells were analyzed by flow cytometry using FL1 channel.

Figure 6A:
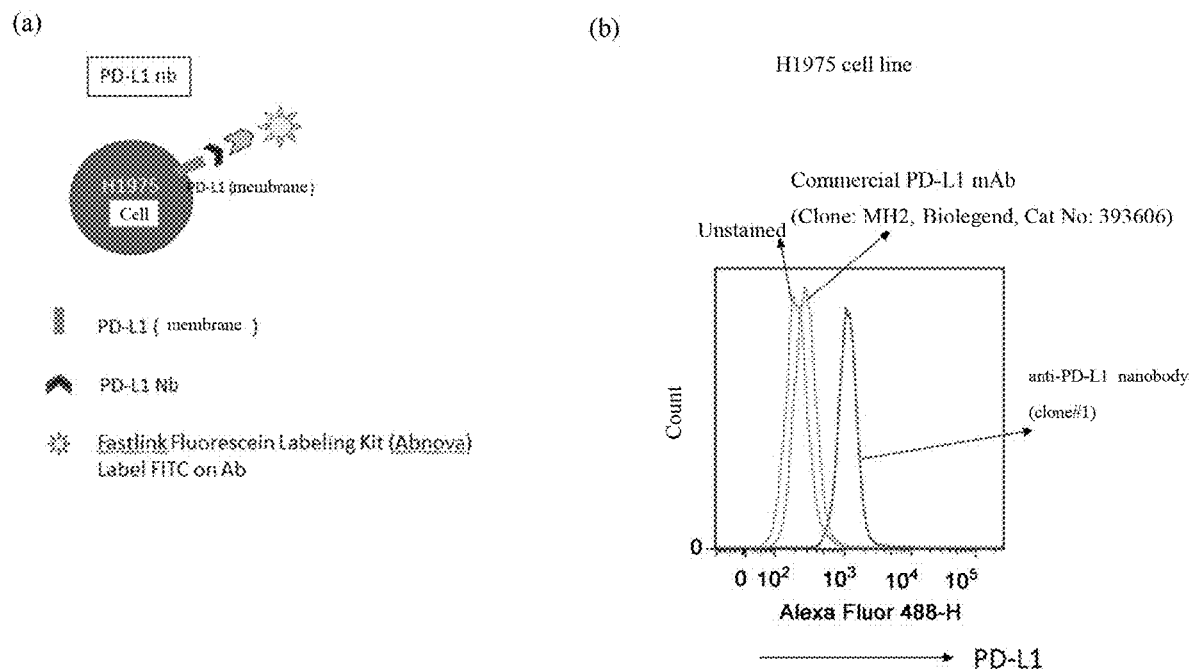
FIGS. 6A and 6B show the result of flow cytometric analysis of the anti-PD-L1 nanobody, wherein nb in (a) of FIG. 6A represents nanobody, Ab represents antibody, FITC represents fluorescein isothiocyanate, mAb in (b) of FIG. 6A represents monoclonal antibody, H1975 is a non-small cell lung cancer cell line, Alexa Fluor 488-H is a bright green fluorescent dye that is excited by laser light at 488 nm, A549 in (a) of FIG. 6B is a non-small cell lung cancer cell line, and MDA-MB-231 in (b) of FIG. 6B is a human breast cancer cell line.
Figure 6B:
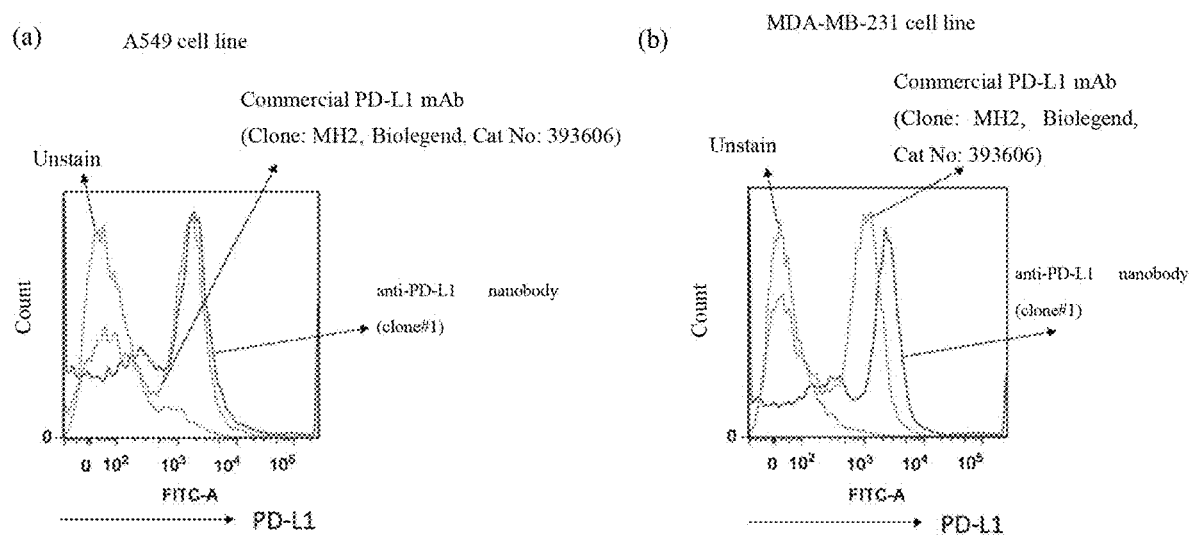

The result of flow cytometric analysis of the anti-PD-L1 nanobody is shown in FIGS. 6A and 6B, wherein nb in (a) of FIG. 6A represents nanobody, Ab represents antibody, FITC represents fluorescein isothiocyanate, mAb in (b) of FIG. 6A represents monoclonal antibody, H1975 is a non-small cell lung cancer cell line, Alexa Fluor 488-H is a bright green fluorescent dye that is excited by laser light at 488 nm, A549 in (a) of FIG. 6B is a non-small cell lung cancer cell line, and MDA-MB-231 in (b) of FIG. 6B is a human breast cancer cell line. The result of this example shows that the anti-PD-L1 nanobody clone #1 (labeled with fluorescein) can be used to detect the expression of PD-L1 in cell samples by flow cyometry analysis.

Example 8

Immunocytochemistry Result of Anti-PD-L1 Nanobody

In this example, the procedures of immunocytochemistry of anti-PD-L1 nanobody are as follows. Tumor cells ($1\times10^5$) were seeded on coverslips in a 6-well plate, incubated overnight. After the indicated treatments, cells were fixed in 1% paraformaldehyde, washed with PBS, permeabilized using 0.1% Triton X-100 in PBS containing 0.5% BSA for 30 min, blocked with 2% BSA, and incubated with specific antibodies in 2% BSA/PBS containing 0.05% Tween-20 (PBST). After washing, the cells were incubated with fluorescein-conjugated secondary antibodies, washed with PBST, and mounted using a water-based mounting medium containing an anti-fade agent and 4',6-diamidino-2-phenylindole (DAPI). Images were analyzed under a Leica TCS SP8 X confocal microscope (Leica).

Figure 7:
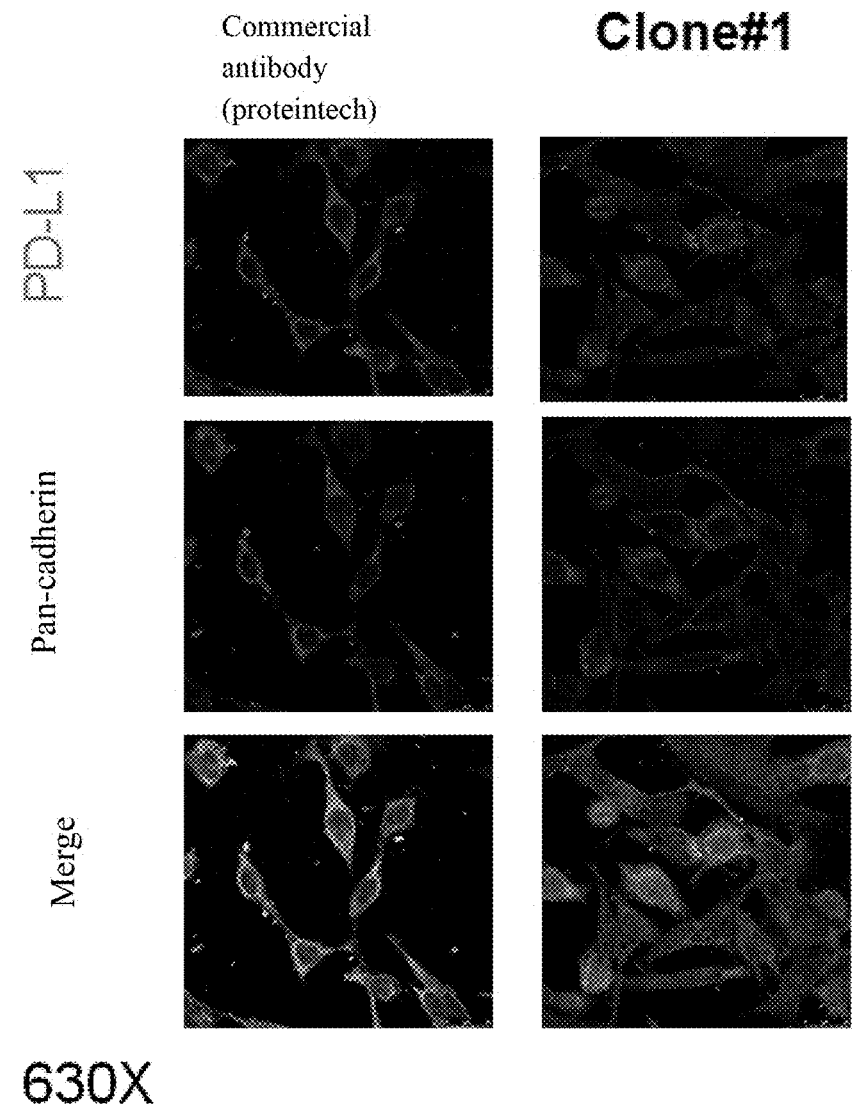
FIG. 7 shows the immunocytochemistry result of the anti-PD-L1 nanobody, wherein the concentration of the anti-PD-L1 nanobody is 1 ng/ml, the secondary antibody is anti-VHH-fluorescein (FITC)(1:5000), pan-cadherin is a cell membrane marker, so that the colocalization of pan-cadherin and PD-L1 can be used to explain membrane-bound PD-L1 is detected by the specific nanobody.

The immunocytochemistry result of anti-PD-L1 nanobody is shown in FIG. 7, wherein H1975 is a non-small cell lung cancer cell line, the concentration of the anti-PD-L1 nanobody is 1 ng/ml, the secondary antibody is anti-VHH-fluorescein (FITC)(1:5000), pan-cadherin is a cell membrane marker, so that the colocalization of pan-cadherin and PD-L1 can be used to explain membrane-bound PD-L1 is detected by the specific nanobody. The result of this example shows that the anti-PD-L1 nanobody clone #1 can be used to detect the expression of PD-L1 in cell samples by flow cytometry analysis.

In summary, the anti-immune-checkpoint nanobody of the present invention effectively binds to PD-L1 protein within the $K_D$ as 0.27 and 0.41 nM, respectively, by surface plasmon resonance binding assay (SPR binding assay), blocks PD-L1/PD-1 signaling in the PD-L1, APC/PD-1 effector co culture system (the PD-L1/PD-1 axis blockade of the anti-PD-L1 nanobody is determined by PD-1/PD-L1 Blockade Bioassay kit), enhances γδ T cell-induced cytotoxicity to tumor cells (MDA-MB-231), restores OKT3 (anti-CD3 monoclonal antibody)-induced T cell perliferation after PD-L1 engagement by Western blotting, and can be used to detect the expression of PD-L1 in cell samples by flow cytometry analysis and immunocytochemistry analysis, thereby achieving the effect of treating cancer and immune-related disorders. In particular, compared with the conventional antibodies, which have the disadvantages of low yield and poor effect, the gene must be transfected into cells by a vector to express the antibody function, the anti-immune-checkpoint nanobody of the present invention can be prepared in vitro on a large scale, and directly administered to the individual in need for treatment. In addition, the present invention can also achieve the effect of detecting the expression level of PD-L1.

Although the present invention has been described with reference to the preferred embodiments, it will be apparent to those skilled in the art that a variety of modifications and changes in form and detail may be made without departing from the scope of the present invention defined by the appended claims.

What is claimed is:

1. An anti-immune-checkpoint nanobody that specifically binds to a programmed cell death ligand 1 (PD-L1), consisted of the amino acid sequence of SEQ ID NO: 1 or SEQ ID NO: 3; wherein the anti-immune-checkpoint nanobody is produced and purified from *Escherichia coli* (*E. coli*) strain HB2151.

2. The anti-immune-checkpoint nanobody according to claim 1, wherein the amino acid sequence is an amino acid sequence of a heavy chain variable domain (VHH) of the anti-immune-checkpoint nanobody.

3. The anti-immune-checkpoint nanobody according to claim 2, which is conjugated with a fragment crystallizable region (Fc region).

4. The anti-immune-checkpoint nanobody according to claim 3, which is conjugated with a second antibody to form a bispecific T-cell engager (BiTE), triple specific T-cell engager (TriTE), bispecific killer cell enager (BiKE), triple specific killer cell engager (TriKE), or any bispecific antibody.

5. The anti-immune-checkpoint nanobody according to claim 4, which blocks interaction and/or binding of the PD-L1 with a receptor of the PD-L1.

6. The anti-immune-checkpoint nanobody according to claim 5, wherein the receptor is programmed cell death protein-1 (PD-1).

7. An isolated nucleic acid encoding the anti-immune-checkpoint nanobody according to claim 1, wherein the isolated nucleic acid consists of the nucleotide sequence of SEQ ID NO: 4 or SEQ ID NO: 6.

8. The isolated nucleic acid according to claim 7, wherein the anti-immune-checkpoint nanobody is conjugated with a fragment crystallizable region (Fc region).

9. The isolated nucleic acid according to claim 8, wherein the anti-immune-checkpoint nanobody is conjugated with a second antibody to form a bispecific T-cell engager (BiTE), triple specific T-cell engager (TriTE), bispecific killer cell enager (BiKE), triple specific killer cell engager (TriKE), or any bispecific antibody.

10. The isolated nucleic acid according to claim 9, wherein the anti-immune-checkpoint nanobody blocks interaction and/or binding of the PD-L1 with a receptor of the PD-L1.

11. The isolated nucleic acid according to claim 10, wherein the receptor is programmed cell death protein-1 (PD-1).

12. A pharmaceutical composition, comprising the anti-immune-checkpoint nanobody according to claim 1 and a pharmaceutically acceptable carrier.

13. The pharmaceutical composition according to claim 12, wherein the amino acid sequence is an amino acid sequence of a heavy chain variable domain (VHH) of the anti-immune-checkpoint nanobody.

14. The pharmaceutical composition according to claim 13, wherein the anti-immune-checkpoint nanobody is conjugated with a fragment crystallizable region (Fc region).

15. The pharmaceutical composition according to claim 14, wherein the anti-immune-checkpoint nanobody is conjugated with a second antibody to form a bispecific T-cell engager (BiTE), triple specific T-cell engager (TriTE), bispecific killer cell enager (BiKE), triple specific killer cell engager (TriKE), or any bispecific antibody.

16. The pharmaceutical composition according to claim 15, wherein the anti-immune-checkpoint nanobody blocks interaction and/or binding of the PD-L1 with a receptor of the PD-L1.

17. The pharmaceutical composition according to claim 16, wherein the receptor is programmed cell death protein-1 (PD-1).

18. A method for detecting expression levels of PD-L1, comprising administering to a biological sample the anti-immune-checkpoint nanobody according to claim 1.

19. The method according to claim 18, wherein the biological sample is blood, urine, sputum, saliva or body fluid.

* * * * *